United States Patent [19]

Kojima et al.

[11] 4,360,589

[45] Nov. 23, 1982

[54] COLOR PHOTOGRAPHIC LIGHT-SENSITIVE MATERIALS

[75] Inventors: Tetsuro Kojima; Masakazu Morigaki; Tsutomu Hamaoka; Satoru Sawada, all of Minami-ashigara, Japan

[73] Assignee: Fuji Photo Film Co., Ltd., Kanagawa, Japan

[21] Appl. No.: 263,805

[22] Filed: May 14, 1981

[30] Foreign Application Priority Data

May 14, 1980 [JP]   Japan ................................ 55-63528

[51] Int. Cl.$^3$ ................................................ G03C 1/40
[52] U.S. Cl. ................................. 430/551; 430/552; 430/554
[58] Field of Search ................ 430/551, 372, 552-555
[56] References Cited

U.S. PATENT DOCUMENTS

| | | | |
|---|---|---|---|
| 3,764,337 | 10/1973 | Arai et al. | 430/551 |
| 4,159,910 | 7/1979 | Fujiwhara et al. | 430/372 |
| 4,174,220 | 11/1979 | Taguchi et al. | 430/551 |
| 4,178,184 | 12/1979 | Taguchi et al. | 430/551 |
| 4,268,621 | 5/1981 | Ogi et al. | 430/551 |

*Primary Examiner*—J. Travis Brown

*Attorney, Agent, or Firm*—Sughrue, Mion, Zinn, Macpeak & Seas

[57] ABSTRACT

A compound represented by the structural formula:

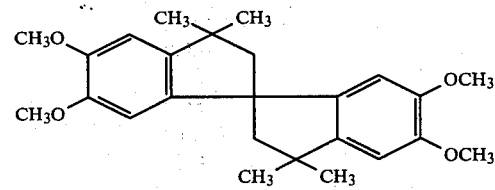

is representative of the compounds disclosed which are utilized within the silver halide layer of photographic light-sensitive materials. The compounds aid in preventing the fading of dye images which are formed by development of color photographic light-sensitive materials as well as aiding in the prevention of discoloration of non-developed areas. The effects of the compounds are particularly noticeable when utilized in combination with magenta couplers or cyan couplers, and other antifading agents in an amount of 2 to 150% by weight based on the weight of the couplers.

9 Claims, No Drawings

COLOR PHOTOGRAPHIC LIGHT-SENSITIVE MATERIALS

FIELD OF THE INVENTION

The present invention relates to color photographic light-sensitive materials and, particularly, to prevention of fading of dye images finally obtained by developing color photographic light-sensitive materials and prevention of discoloration of nondeveloped parts (referred to as white area, hereinafter).

BACKGROUND OF THE INVENTION

Generally, dye images obtained by the photographic processing of silver halide color photographic light-sensitive materials are composed of azometine dyes or indoaniline dyes formed by reactions of an oxidation product of an aromatic primary amine developing agent with couplers. The color photographic images thus obtained are not always stabilized to light, humidity or temperature, and fading or discoloration of dye images and discoloration of the white area result in deterioration of quality of images when they are exposed to light for a long period of time or preserved at a high temperature and high humidity.

Such fading and discoloration of the images are fatal faults for recording materials. Examples of methods for eliminating these defects include the use of couplers which cause less fading, the use of antifading agents to prevent fading by light, and the use of ultraviolet ray absorbing agents for preventing deterioration of images by ultraviolet rays.

For example, there are couplers described in U.S. Pat. No. 3,519,429, wherein a light fading prevention group is bonded. Examples of antifading agents having a phenolic hydroxy group or a group capable of forming the phenolic hydroxy group by hydrolysis include bisphenols described in Japanese Patent Publication No. 31256/73 and U.S. Pat. No. 2,991,177, hydroquinones and α-tocopherol described in U.S. Pat. No. 2,360,290, 6-hydroxychromans described in U.S. Pat. No. 3,432,300, 5-hydroxycoumarans described in U.S. Pat. No. 3,573,050, pyrogallol, gallic acid and esters thereof described in U.S. Pat. No. 3,069,262, and 6,6'-dihydroxy-2,2-bisspirochromans described in U.S. Pat. No. 3,764,337.

Examples of antifading agents wherein hydrogen of the phenolic hydroxy group is substituted by an alkyl group, etc., include compounds described in U.S. Pat. No. 4,159,910 derived from the above described 6,6'-dihydroxy-2,2-bisspirochroman, ether derivatives of 6-hydroxychroman and 5-hydroxychroman described in Japanese Patent Application (OPI) No. 17729/78 and ether derivatives derived from catechols described in Japanese Patent Application (OPI) Nos. 145530/79 and 21004/80.

These compounds do aid in the prevention of fading or discoloration of dye images. However, they are insufficient to satisfy the requirements of consumers who demand high quality images. They are unable to produce an overall excellent color photograph. Their defects include a change of color hue, occurrence of fogs, and inferior dispersion or formation of fine crystals after application of emulsions.

SUMMARY OF THE INVENTION

An object of the present invention is to provide color photographic light-sensitive materials. The photographic light-sensitive layer of the materials contain a dye image stabilizer which aids in the prevention of fading or discoloration of dye images without causing a change of color hue or occurrence of fogs. Furthermore, the dye image stabilizer does not form fine crystals after application. The material forms color images which do not change their color for a long period of time. Furthermore, color contamination of the white area is remarkably prevented.

Another object of the present invention is to provide color photographic antifading agents which have excellent solubility in solvents having a high boiling point, do not form fine crystals before and after application and do not have a bad influence upon other photographic additives.

As a result of various studies, the present inventors have found that the objects of the present invention are attained by incorporating a compound represented by the following formula (I) in a photographic layer of silver halide color photographic light-sensitive materials.

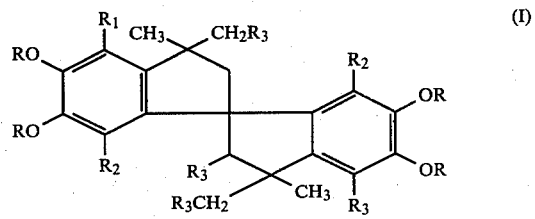

In the formula R represents an alkyl group (for example, methyl, ethyl, propyl, n-octyl, tert-octyl, or hexadecyl), an aralkyl group (for example, benzyl), an alkenyl group (for example, allyl, octenyl or oleyl), an aryl group (for example, phenyl or naphthyl), a heterocyclic group (for example, tetrahydropyranyl or pyrimidyl), or a group represented by $R_4CO-$, $R_5SO_2-$ or $R_6NHCO-$, wherein $R_4$, $R_5$ and $R_6$ represent each an alkyl group (for example, methyl, ethyl, n-propyl, n-butyl, n-octyl, or tert-octyl), an aralkyl group (for example, benzyl), an alkenyl group (for example, allyl, octenyl or oleyl), an aryl group (for example, phenyl, methoxyphenyl or naphthyl) or a heterocyclic group (for example, pyridyl or pyrimidyl), $R_1$ and $R_2$ independently represent each hydrogen, a halogen atom (for example, fluorine, chlorine or bromine), an alkyl group (for example, methyl, ethyl, or n-butyl), an aralkyl group (for example, benzyl), an alkenyl group (for example, allyl, hexenyl or octenyl), an alkoxy group (for example, methoxy, ethoxy or benzyloxy) or an alkenoxy group (for example, 2-propenyloxy or hexenyloxy). $R_3$ represents hydrogen, an alkyl group (for example, methyl, ethyl, or n-butyl), an aralkyl group (for example, benzyl), an alkenyl group (for example, 2-propenyl, hexenyl or octenyl) or an aryl group (for example, phenyl, methoxyphenyl, chlorophenyl or naphthyl).

DETAILED DESCRIPTION OF THE INVENTION

The compounds represented by the formula (I) is effective when R represents an alkyl group or an alkenyl group, and it is particularly effective when R represents an alkyl group or an alkenyl group, and in addition, either one of $R_1$ and $R_2$ represents hydrogen.

The compounds represented by the formula (I) of the present invention are obtained from ketones and catechols. They are generally obtained by substituting a phenolic hydroxyl group of 5,6,5',6'-tetrahydroxy-1,1'-bisspiroindane used as a gelatin hardenable developing agent for black-and-white photographic systems. The antifading effect of the compounds represented by the formula (I) is remarkably superior to that of 6,6'-hydroxy-2,2'-bisspirochroman obtained from ketones and hydroquinones (described in U.S. Pat. No. 3,764,337) and that of derivatives thereof wherein the phenolic hydroxy group is substituted (described in U.S. Pat. No. 4,159,910). This fact means that an industrial utility value of the compounds which have been used as only the gelatin hardenable developing agent is remarkably enhanced.

The compounds represented by the formula (I) is particularly effective for preventing fading and discoloration of white area when they are used together with magenta couplers, particularly 5-pyrazolone type couplers, or cyan couplers, particularly phenol or naphthol derivatives.

Moreover, the compounds represented by the formula (I) is further effective when they are used together with known antifading agents such as hydroquinone derivatives, hydroxychroman derivatives, hydroxyspirochroman derivatives, derivatives of hydroxychroman or hydroxyspirochroman wherein the hydroxy group is converted into an alkoxy group, or alkoxy phenol derivatives.

The dye image stabilizers represented by the formula (I) used in the present invention are preferable used in an amount of the range of 0.5 to 200% by weight, more preferably 2 to 150% by weight, based on couplers, though the added amounts depend on the kind of couplers.

Typical examples of these compounds are described below. However, compounds used in the present invention are not limited to them.

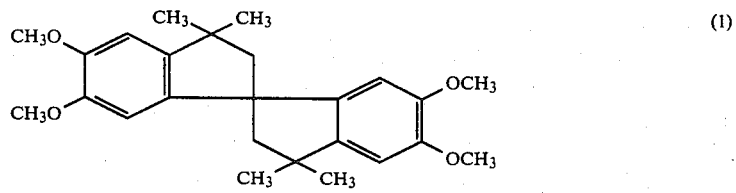 (1)

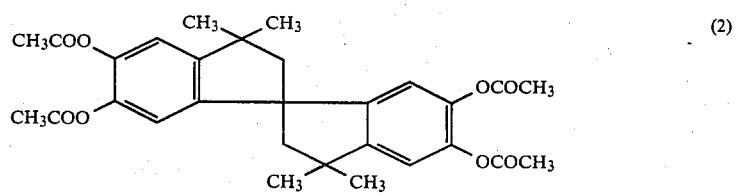 (2)

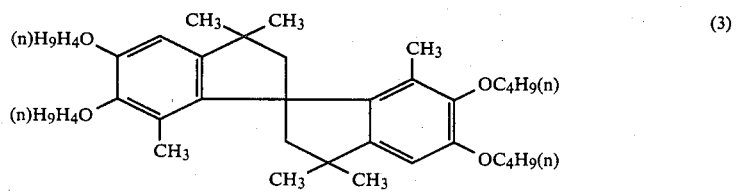 (3)

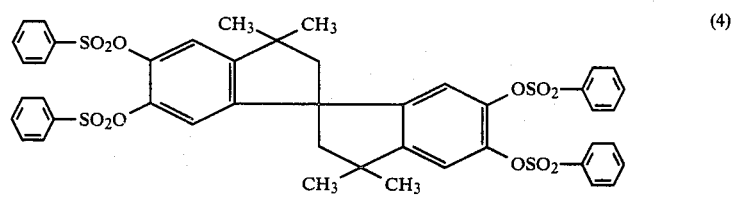 (4)

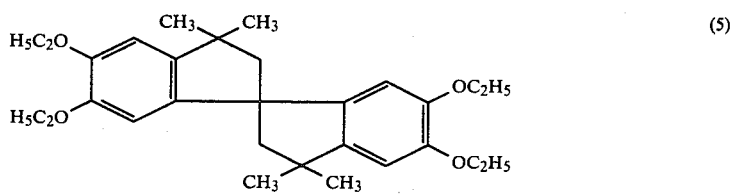 (5)

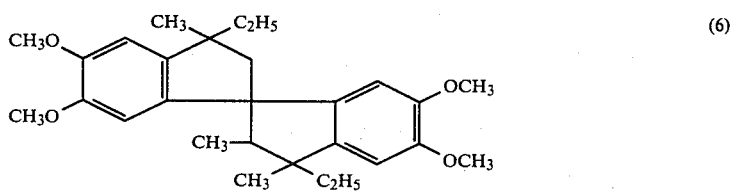 (6)

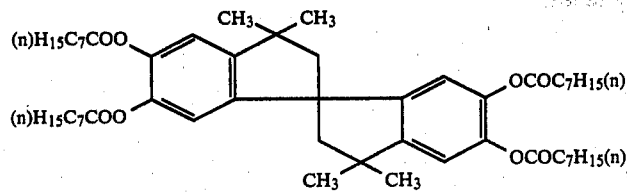
(7)
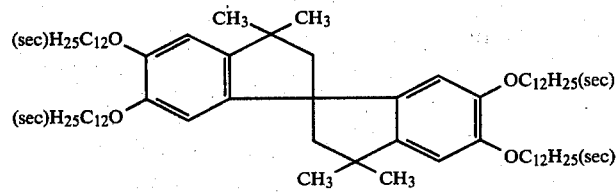
(8)
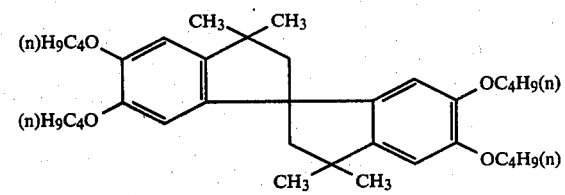
(9)
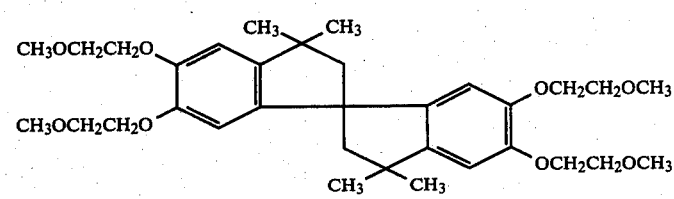
(10)
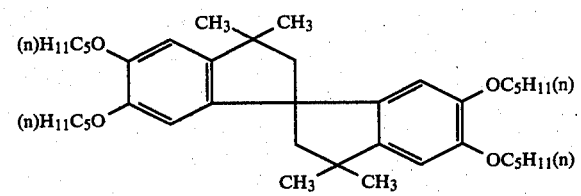
(11)
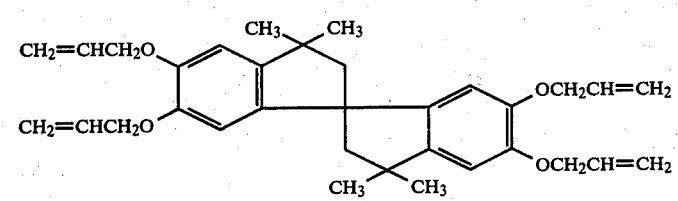
(12)
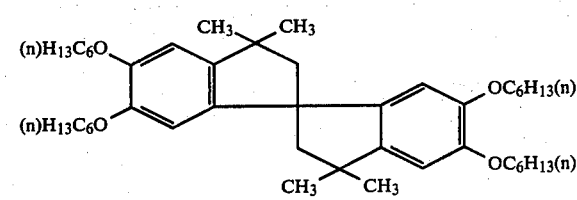
(13)
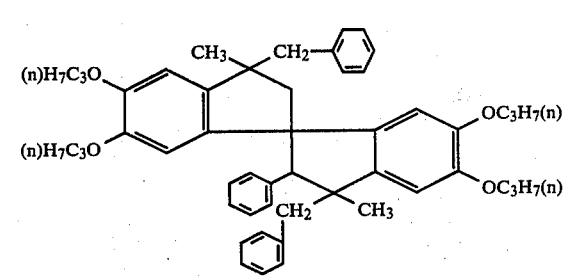
(14)

-continued
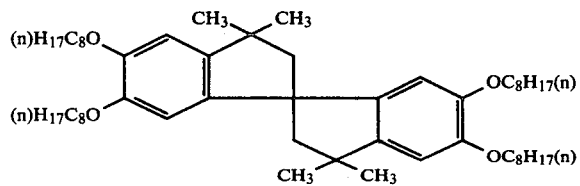 (15)
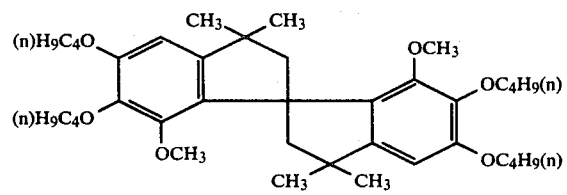 (16)
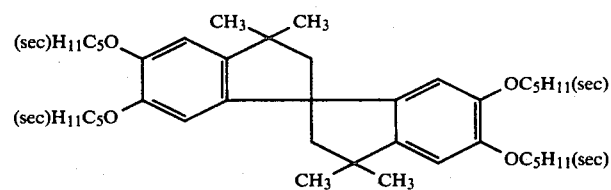 (17)
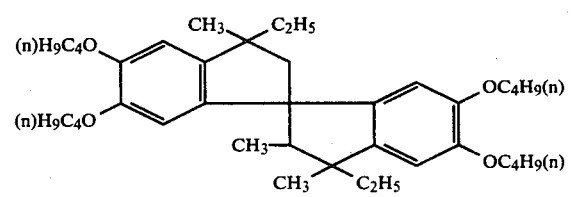 (18)
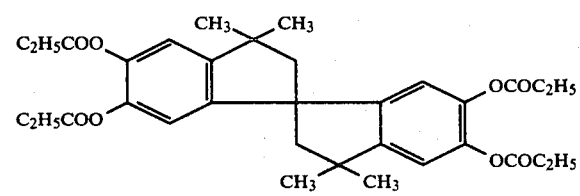 (19)
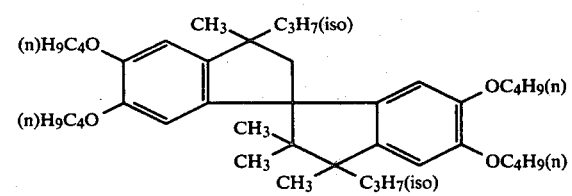 (20)
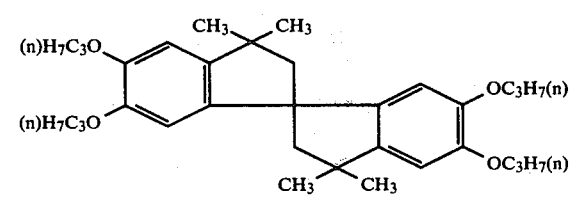 (21)
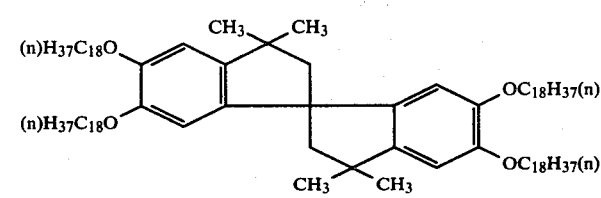 (22)

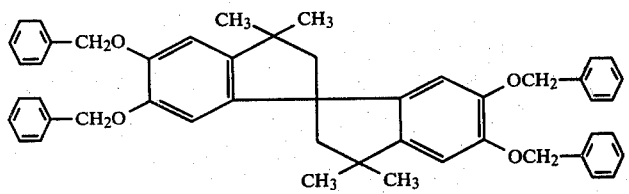 (23)

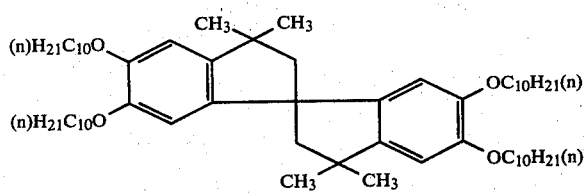 (24)

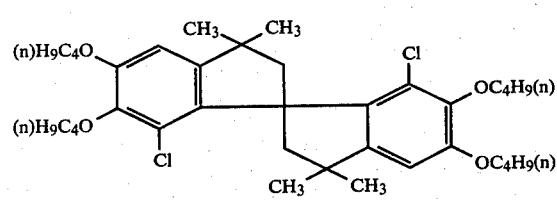 (25)

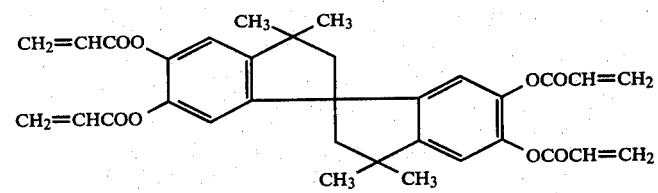 (26)

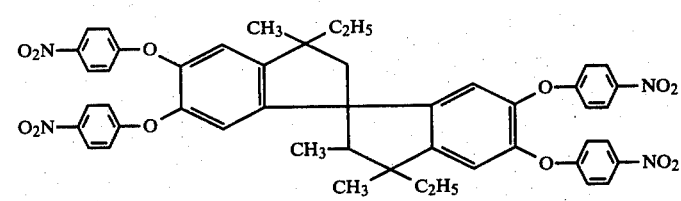 (27)

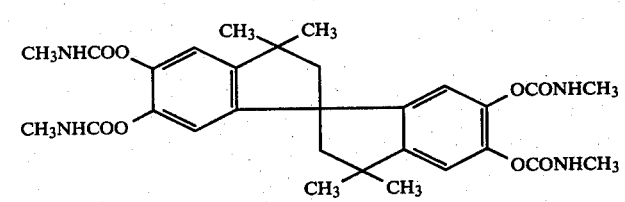 (28)

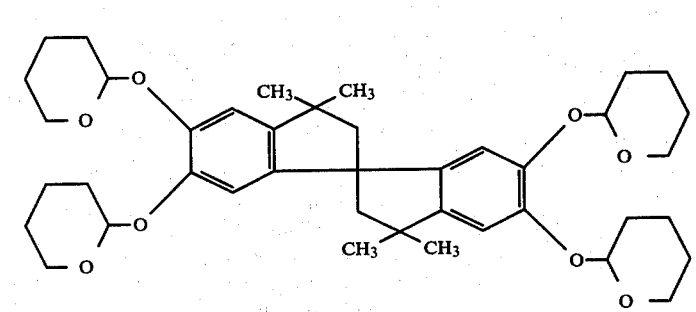 (29)

The 5,6,5',6'-tetrahydroxy-1,1'-spirobisindane compounds used in the present invention can be synthesized according to the process described in "Journal of Chemical Society" 1934, page 1678 incorporated herein by reference. Further, the compounds in the present invention can be synthesized by alkylation or esterification of 5,6,5',6'-tetrahydroxy-1,1'-spirobisindane compounds by conventional processes.

In the following, examples of synthesizing typical compounds are shown, but other compounds can be synthesized by the same process.

Synthesis 1

Synthesis of 5,6,5',6'-tetrahydroxy-3,3,3',3'-tetramethyl-1,1'-spirobisindane (Compound No. 1)

34.1 g (0.1 mol) of 5,6,5',6'-tetrahydroxy-3,3,3',3'-tetramethyl-1,1'-spirobisindane was dissolved in 100 ml of dimethylformamide. After adding 41.5 g (0.3 mol) of potassium carbonate, the mixture was heated to 35° C. To the resulting mixture, 85.2 g (0.6 mol) of methyl iodide was added dropwise and the mixture was stirred at 35° C. for 3 hours. After conclusion of the reaction, the reaction mixture was poured into 2 liters of ice water to obtain crude crystals. When these crude crystals were recrystallized with methyl alcohol, white crystals having a melting point of 125° to 126° C. were obtained (Yield: 33.8 g, 85.2%).

Elementary analysis value: C: 75.95%; H: 8.14%; Calculation value: C: 75.73%; H: 8.13%.

Synthesis 2

Synthesis of 5,6,5',6'-tetraacetoxy-3,3,3',3'-tetramethyl-1,1'-spirobisindane (Compound No. 2)

34.1 g (0.1 mol) of 5,6,5',6'-tetrahydroxy-3,3,3',3'-tetramethyl-1,1'-spirobisindane was dissolved in 500 ml of acetic anhydride. After adding 200 g (2.43 mols) of sodium acetate, the mixture was heated to 90° C. and stirred for 3 hours. After conclusion of the reaction, the reaction mixture was poured into 2 liters of ice water to obtain crude crystals. When the crude crystals were recrystallized with methyl alcohol, white crystals having a melting point of 171° to 172° C. were obtained (Yield: 38.3 g, 75.2%).

Elementary analysis value: C: 68.61%; H: 6.38%; Calculation value: C: 68.49%; H: 6.34%.

Synthesis 3

Synthesis of 5,6,5',6'-tetrabutoxy-3,3,3',3'-tetramethyl-1,1'-spirobisindane (Compound No. 9)

17.1 g (0.05 mol) of 5,6,5',6'-tetrahydroxy-3,3,3',3'-tetramethyl-1,1'-spirobisindane was dissolved in 50 ml of dimethylformamide. After adding 20.8 g (0.15 mol) of potassium carbonate, the mixture was heated to 70° C. To the mixture, 41.1 g (0.3 mol) of n-butyl bromide was added dropwise, and the mixture was stirred at 70° C. for 5 hours. The reaction mixture was poured into 1 liter of water and extracted with 1 liter of ethyl acetate. After drying to an organic layer with anhydrous sodium sulfate, the solvent was distilled off under a reduced pressure, by which a crystalline residue was obtained. When it was recrystallized with methyl alcohol, white crystals having a melting point of 50° to 51° C. were obtained (Yield: 24.1 g, 85.5%).

Elementary analysis value: C: 78.79%; H: 9.96%; Calculation value: C: 78.68%; H: 9.99%.

EXAMPLE 1

10 g of a magenta coupler: 1-(2,4,6-trichlorophenyl)-3-[(2-chloro-5-tetradecaneamido)anilino]-2-pyrazoline-5-one was dissolved in 20 ml of tricresyl phosphate and 20 ml of ethyl acetate. The resulting solution was dispersed by emulsifying in 80 g of a solution of gelatin containing 8 ml of a 1% aqueous solution of sodium dodecylbenzenesulfonate.

The resulting emulsified dispersion was then mixed with 145 g (7 g as Ag) of a green-sensitive silver chlorobromide emulsion (Br 50% by mol), and sodium dodecylbenzenesulfonate was added as a coating assistant. The emulsified dispersion was applied to a paper base the both surfaces of which were laminated with polyethylene.

The amount of the coupler was 400 mg/m². To the layer, a gelatin protective layer (gelatin: 1 g/m²) was applied to produce Sample A.

Sample B to J were produced by the same process as that for producing Sample A, except that compounds of the present invention and comparative compounds were used in preparation of the above described emulsified emulsion as shown in Table 1.

These samples were exposed to light at 1000 luxes for 1 second and subsequently processed with the following processing solutions.

| Developing solution: | | |
|---|---|---|
| Benzyl alcohol | | 15 ml |
| Diethylenetriaminepentaacetic acid | | 5 g |
| KBr | | 0.4 g |
| $Na_2SO_3$ | | 5 g |
| $Na_2CO_3$ | | 30 g |
| Hydroxyamine sulfate | | 2 g |
| 4-Amino-3-methyl-N—β-(methanesulfonamido)ethylaniline · $3/2H_2SO_4 \cdot H_2O$ | | 4.5 g |
| Water to make | | 1000 ml |
| | pH | 10.1 |
| Bleach-fixation solution: | | |
| Ammonium thiosulfate (70 wt. %) | | 150 ml |
| $Na_2SO_3$ | | 5 g |
| As[Fe(EDTA)] | | 40 g |
| EDTA | | 4 g |
| Water to make | | 1000 ml |
| | pH | 6.8 |

| Processing step | Temperature | Time |
|---|---|---|
| Developing solution | 33° C. | 3 minutes and 30 seconds |
| Bleach-fixation solution | 33° C. | 1 minute and 30 seconds |
| Water wash | 28 to 35° C. | 3 minutes |

Each sample on which a dye image was formed as described above was subjected to a fading test by means of a xenon tester (illuminance: 200,000 luxes) for 5 days with putting an ultraviolet ray absorbing filter produced by Fuji Photo Film Co. which cut rays of less than 400 nm. The measurement was carried out by a Macbeth densitometer Type RD-514 (status AA filter), and a change of density on the part having an initial density of 2.0 and a change of density on the white area were measured.

TABLE I

| Sample | Color Image Stabilizer | Amount Added (g) | Change of Yellow Density on White Area | Change of Magenta Density (Initial Density: 2.0) | Note |
|---|---|---|---|---|---|
| A | — | — | +0.27 | −1.42 | Comparative Example |

TABLE I-continued

| Sample | Color Image Stabilizer | Amount Added (g) | Change of Yellow Density on White Area | Change of Magenta Density (Initial Density: 2.0) | Note |
|---|---|---|---|---|---|
| B | Compound (1) | 3 | +0.10 | −0.20 | Present Invention |
| C | Compound (3) | 4.5 | +0.11 | −0.25 | Present Invention |
| D | Compound (6) | 3.3 | +0.07 | −0.26 | Present Invention |
| E | Compound (10) | 4.3 | +0.09 | −0.27 | Present Invention |
| F | Compound (23) | 4.4 | +0.10 | −0.25 | Present Invention |
| G | Compound (2) | 3.8 | +0.13 | −0.40 | Present Invention |
| H | Compound (4) | 6.8 | +0.14 | −0.44 | Present Invention |
| I | Comparative Compound (a) | 3.2 | +0.25 | −0.98 | Comparative Example |
| J | Comparative Compound (b) | 4.5 | +0.22 | −0.90 | Comparative Example |

The result of the experiments clearly show that the compounds of the present invention were effective for preventing light fading of color images and they had an effect on preventing yellowing of the white area caused by light.

Comparative compound (a)

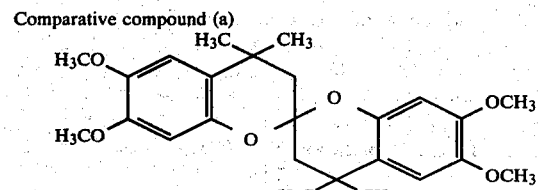

Comparative compound (b)

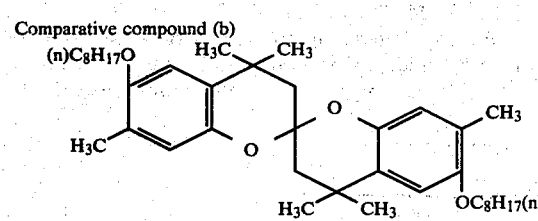

EXAMPLE 2

A coating composition for the third layer described in the following Table III was produced using as a magenta coupler the same compound as in Example 1 according to the process for producing Sample A in Example 1. Then a multilayer sample having a third layer (Sample K) shown in Table III was produced. Further, multilayer samples L to P shown in Table II were produced according to the above described Sample K. These samples were exposed to light and processed by the same manner as in Example 1. Each samples in which dye images were formed was subjected to a fading test for 4 weeks by a fluorescent fading lamp (200,000 luxes). The obtained results are shown in Table II.

The result described in Table II clearly shows that the compounds of the present invention are effective for preventing light fading of color images, when used alone or in combination of the already known antifading agents, and that the effect becomes larger with an increase in the amount added or by using the compounds together with a known antifading agent such as Comparative compound (c).

Comparative compound (c)

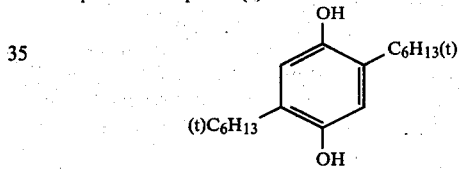

TABLE II

| Sample | Color Image Stabilizer | Amount Added Coupler 10 g | Change of Magenta Density (Initial Density: 1.0) | Note |
|---|---|---|---|---|
| K | — | — | −0.84 | Comparative Example |
| L | Compound (1) | 3 g | −0.14 | Present Invention |
| M | Compound (6) | 3.3 g | −0.12 | Present Invention |
| N | Comparative Compound (a) | 3.2 g | −0.41 | Comparative Example |
| O | Comparative Compound (b) | 4.5 g | −0.29 | Comparative Example |
| P | Compound (1) Comparative Compound (c) | 3 g 3 g | −0.09 | Present Invention |

TABLE III

| | |
|---|---|
| The 6th Layer (Protection Layer) | Gelatin (coated amount: 1000 mg/m$^2$) |
| The 5th Layer (Red-Sensitive Layer) | Silver chlorobromide emulsion (Br: 50% by mol, coated amount: silver 300 mg/m$^2$) Cyan coupler (*1) (coated amount: 400 mg/m$^2$) Solvent for coupler (*2) (coated amount: 200 mg/m$^2$) Gelatin (coated amount: 1000 mg/m$^2$) |
| The 4th Layer (Intermediate Layer) | Gelatin (coated amount: 1200 mg/m$^2$) Ultraviolet ray absorbing agent (*3) (coated amount: 1000 mg/m$^2$) Solvent for ultraviolet ray absorbing agent (*2) (coated amount: 250 mg/m$^2$) |

TABLE III-continued

| | |
|---|---|
| The 3rd Layer (Green-Sensitive Layer) | Silver chlorobromide emulsion (Br: 50% by mol, coated amount: silver 290 mg/m$^2$)<br>Magenta coupler (*4) (coated amount: 200 mg/m$^2$)<br>Solvent for coupler (*5) (coated amount: 200 mg/m$^2$)<br>Gelatin (coated amount: 1000 mg/m$^2$) |
| The 2nd Layer (Intermediate Layer) | Gelatin (coated amount: 1000 mg/m$^2$) |
| The 1st Layer (Blue-Sensitive Layer) | Silver chlorobromide emulsion (Br: 80% by mol, coated amount: silver 400 mg/m$^2$)<br>Yellow coupler (*6) (coated amount: 300 mg/m$^2$)<br>Solvent for coupler (*7) (coated amount: 150 mg/m$^2$)<br>Gelatin (coated amount: 1200 mg/m$^2$) |
| Base | Paper base the both surfaces of which were laminated with polyethylene. |

(*1) Coupler: 2-[α-(2,4-di-tert-pentylphenoxy)-butaneamido]-4,6-dichloro-5-methylphenol
(*2) Solvent: Dibutyl phthalate
(*3) Ultraviolet Ray Absorbing Agent: 2-(2-hydroxy-3-sec-butyl-5-tert-butylphenyl)benzotriazole
(*4) Coupler: 1-(2,4,6-trichlorophenyl)-3-(2-chloro-5-tetradecanamido)anilino-2-pyrazoline-5-one
(*5) Solvent: Tricresyl phosphate
(*6) Coupler: α-Prvaloyl-α-(2,4-dioxo-5,5'-dimethyloxazolidin-3-yl)-2-chloro-5-[α-2,4-di-tert-pentylphenoxy)butanamido]-acetanilide
(*7) Solvent: Dioctylbutyl phosphate.

EXAMPLE 3

Multilayer samples Q to V shown in Table IV were produced with using layer compositions and couplers described in Table III in Example 2 and adding the compound of the present invention or the comparative compound to the 5th layer (red-sensitive layer) according to the process shown in Sample A.

These samples were exposed to light and processed in the same manner as in Example 1. After each sample in which a cyan dye image was formed was exposed to light for 150 hours by a xenon tester, density lowering ratios to the initial density of the cyan dye image were measured. The results are shown in Table IV.

From the results shown in Table IV, it is understood that the compounds of the present invention show a clearly excellent effect for preventing fading of cyan dye images and that the effect if superior to that of antifading agents known hitherto.

TABLE IV

| Sample | Color Image Stabilizer | Amount Added (g)/ Coupler 10 g | Change of Cyan Density ($D_{2.0}$) | Change of Cyan Density ($D_{1.0}$) | Note |
|---|---|---|---|---|---|
| K | — | — | 25% | 34% | Comparative Example |
| Q | Compound (1) | 3 | 10% | 15% | Present Invention |
| R | Compound (6) | 3.3 | 8% | 13% | Present Invention |
| S | Compound (19) | 4.2 | 13% | 16% | Present Invention |
| T | Compound (24) | 6.8 | 10% | 14% | Present Invention |
| U | Comparative Compound (a) | 3.2 | 21% | 29% | Comparative Example |
| V | Comparative Compound (b) | 4.5 | 20% | 25% | Comparative Example |

Emulsion layers of the photographic light-sensitive material produced by the present invention may contain dye image forming couplers, i.e., compounds which form a dye by reacting with an oxidation product of aromatic amine (generally, primary amine) developing agents (referred to as "coupler", hereinafter). Nondiffusible couplers having a hydrophobic group called a ballast group in the molecule are preferably to use. The couplers may be 4-equivalent ones or may be 2-equivalent ones. The couplers may include colored couplers having an effect on color correction and couplers which release a development inhibitor by development (the so-called DIR couplers). The couplers may include those which form a colorless product by a coupling reaction.

Useful yellow forming couplers include known ring-cleavage ketomethylene type couplers. Benzoylacetanilido compounds and pivaloyl acetanilido compounds are examples of preferred yellow forming couplers. Examples of useful yellow forming couplers capable include those described in U.S. Pat. Nos. 2,875,057, 3,265,506, 3,408,194, 3,551,155, 3,582,322, 3,725,072 and 3,891,445, German Pat. No. 1,547,868, German Patent Application (OLS) Nos. 2,219,917, 2,261,361 and 2,414,006, British Pat. No. 1,425,020, Japanese Patent Publication No. 10783/76 and Japanese Patent Application (OPI) Nos. 26133/72, 73147/73, 102636/76, 6341/75, 123342/75, 130442/75, 21827/76, 87650/75, 82424/77 and 115219/77.

Useful magenta forming couplers include pyrazolone compounds, imidazolone compounds and cyanoacetyl compounds with pyrazolone compounds being preferred. Examples of the magenta forming couplers include those described in U.S. Pat. Nos. 2,600,788, 2,983,608, 3,062,653, 3,127,269, 3,227,554, 3,311,476, 3,419,391, 3,519,429, 3,558,319, 3,582,322, 3,615,605, 3,834,908 and 3,891,445, German Pat. No. 1,810,464, German Patent Application (OLS) Nos. 2,408,665, 2,417,945, 2,418,959 and 2,424,467, Japanese Patent Publication No. 6031/65 and Japanese Patent Application (OPI) Nos. 20826/76, 58922/77, 129538/74, 74027/74, 159336/75, 42121/77, 74028/74, 60233/75, 26541/76 and 55122/78.

Useful cyan forming couplers include phenol compounds and naphthol compounds. Examples of the cyan forming couplers include those described in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German Patent Application (OLS) Nos. 2,414,830 and 2,454,329, and Japanese Patent Application (OPI) Nos. 59838/73, 26034/76, 5055/73, 146828/76, 69624/77 and 90932/77.

Useful colored couplers include those described in U.S. Pat. Nos. 3,476,560, 2,521,908 and 3,034,892, Japanese Patent Publication Nos. 2016/69, 22335/63, 11304/67 and 32461/69, Japanese Patent Application (OPI) Nos. 26034/76 and 42121/77, and German Patent Application (OLS) No. 2,418,959.

Useful DIR couplers include described in U.S. Pat. Nos. 3,227,554, 3,617,291, 3,701,783, 3,790,384 and 3,632,345, German Patent Application (OLS) Nos. 2,414,006, 2,454,301 and 2,454,329, British Pat. No. 953,454, Japanese Patent Application (OPI) Nos. 69624/77 and 122335/74 and Japanese Patent Publication No. 16141/76.

Compounds which release a development inhibitor by development may be incorporated in the photographic light-sensitive materials in addition to the DIR couplers. For example, it is possible to use those described in U.S. Pat. Nos. 3,297,445 and 3,379,529, German Patent Application (OLS) No. 2,417,914 and Japanese Patent Application (OPI) Nos. 15271/77 and 9116/78.

Two or more of the above described couplers may be contained in the same layer. The same compound may be contained in two or more layers.

These couplers are generally added in an amount of $2 \times 10^{-3}$ mol to $5 \times 10^{-1}$ mol, preferably $1 \times 10^{-2}$ mol to $5 \times 10^{-1}$ mol, per mol of silver in the emulsion layer.

In carrying out the present invention, it is possible to use the following known antifading agents. Further, the color image stabilizers used in the present invention may be used alone or as a mixture of two or more of them. Useful antifading agents include hydroquinone derivatives described in U.S. Pat. Nos. 2,360,290, 2,418,613, 2,675,314, 2,701,197, 2,704,713, 2,728,659, 2,732,300, 2,735,765, 2,710,801 and 2,816,028 and British Pat. No. 1,363,921; gallic acid derivatives described in U.S. Pat. Nos. 3,457,079 and 3,069,262; p-alkoxyphenols described in U.S. Pat. Nos. 2,735,765 and 3,698,909 and Japanese Patent Publication Nos. 20977/74 and 6623/77; p-oxyphenol derivatives described in U.S. Pat. Nos. 3,432,300, 3,573,050, 3,574,627 and 3,764,337 and Japanese Patent Application (OPI) Nos. 35633/77, 14743/77 and 152225/77; and bisphenols described in U.S. Pat. No. 3,700,455.

A process for introducing the compounds (color image stabilizers) of the present invention into photographic layers of color photographic light-sensitive materials comprises: dissolving the compounds in an organic solvent having a low boiling point such as ethyl acetate or ethanol; and adding directly the resulting solution to a silver halide emulsion or a mixture thereof with a coupler dispersion without emulsifying. However, it is preferable to use a process which comprises: dissolving the compounds (color image stabilizers) of the present invention in a solvent having a high boiling point such as dibutylphthalate or tricresylphosphate, together with couplers in the presence of, if necessary, an auxiliary solvent having a low boiling point; dispersing the resulted solution in a water soluble protective colloid such as gelatin; and adding the resulting emulsified dispersion to a silver halide emulsion. An alternative method involves preparing an emulsified dispersion of the color image stabilizers of the present invention and adding the emulsified dispersion in a silver halide emulsion together with a coupler dispersion.

As photographic layers to which the compounds (color image stabilizers) of the present invention are added include coupler-contained silver halide photographic light-sensitive emulsion layers (for example, red-sensitive silver halide emulsion layers, green-sensitive, silver halide emulsion layers and blue-sensitive silver halide emulsion layers), and photographic light-insensitive auxiliary layers adjacent thereto (for example, protective layers, filter layers, intermediate layers and subbing layers) and image receiving layers for a color diffusion transfer photographic material. It is particularly preferred to add the color image stabilizers of the present invention to a photographic layer containing a magenta coupler because this is particularly effective in preventing fading or discoloration of magenta images.

Examples of organic solvents having a high boiling point which are useful for dispersing the color image stabilizers of the present invention alone or together with couplers include compounds such as butyl phthalate, dinonyl phthalate, butyl benzoate, diethylhexyl sebacate, butyl stearate, dinonyl maleate, tributyl citrate, tricresyl phosphate, dioctylbutyl phosphate, trihexyl phosphate or trioctadecyl phosphate, as described in U.S. Pat. No. 3,676,137; diethyl succinate, dioctyl adipate, 3-ethylbiphenyl; and liquid dye stabilizers described as "Improvement type photographic dye image stabilizer" in Product Licensing Index Vol. 83, pages 26-29 (March, 1971).

Examples of organic solvents having a low boiling point used as auxiliary solvents together with the organic solvents having a high boiling point include ethyl acetate, butyl acetate, ethyl propionate, ethyl formate, butyl formate, nitroethane, carbon tetrachloride, chloroform, hexane, cyclohexane, ethylene glycol, acetone, ethanol, dimethylformamide and dioxane. Further, benzene, toluene or xylene may be added to these solvents.

Examples of surface active agents used for dispersing the color image stabilizers of the present invention alone or the aqueous protective colloid solution of them prepared by dissolving together with couplers include saponin, sodium alkylsulfosuccinate and sodium alkylbenzenesulfonate. Examples of the hydrophilic colloids include gelatin (lime-processed gelatin or acid-processed gelatin), casein, carboxymethyl cellulose, polyvinyl alcohol, polyvinylpyrrolidone, styrene-maleic acid anhydride copolymer, condensate of styrene-maleic acid anhydride copolymer and polyvinyl alcohol, polyacrylic acid salts, and ethylcellulose. However, the present invention is not limited to them.

Useful bases include cellulose nitrate films, cellulose acetate films, cellulose acetate butyrate films, cellulose acetate propionate films, polystyrene films, polyethylene terephthalate films, polycarbonate films and laminates thereof, thin glass films and paper of the type which is generally used for photographic light-sensitive materials. Good results are also obtained by using bases such as coated or laminated paper prepared by using barita or α-olefin polymers, particularly polymers of α-olefin having 2 to 10 carbon atoms such as polyethylene, polypropylene or ethylene-butene copolymer, and plastic films the surface of which was matted to improve adhesive property to other high molecular materials a shown in Japanese Patent Publication No. 19068/72.

From these bases, a transparent base or an opaque base is selected according to the purpose of the photographic light-sensitive material. Further, they may be colored (while remaining transparent) by adding dyes or pigments.

Useful opaque bases include paper and bases prepared by adding dyes or pigments such as titanium oxide to transparent films, plastic films the surface of which was processed by a process described in British Pat. No. 1,237,475, and paper and plastic films which have a completely light-intercepting property prepared by adding carbon black or dyes. The bases are usually provided with a subbing layer. In order to further improve the adhesive property, the surface of the bases may be subjected to preliminary processing such as corona discharging, ultraviolet ray application or flame treatment.

In a preferred embodiment of the present invention, an ultraviolet ray absorbing layer is provided on a photographic light-sensitive emulsion layer as an image forming layer. This effectively prevents fading and discoloration caused by light.

The present invention is not restricted to the use of any particular conventional color processing agents such as color developers, bleaching agents or fixing agents. The present invention can be advantageously used for silver economy type color photographic light-sensitive materials described in U.S. Pat. No. 3,902,905. The present invention is not restricted to using any particular kind of intensifiers for color intensification processing as described in German Patent Application (OLS) No. 181,390, Japanese Patent Application (OPI) No. 9728/73 and Japanese Patent Publication No. 14625/77.

The color photographic light-sensitive materials capable of applying the present invention include conventional color photographic light-sensitive materials and, particularly, color photographic materials for printing. However, the compounds of the invention may also be used for color photographic processes described in U.S. Pat. Nos. 3,227,550, 3,227,551 and 3,227,552 and U.S. Provisional Patent No. B351,673, and particularly a color diffusion transfer photographic process.

In order to obtain dye images on the color photographic light-sensitive materials of the present invention, it is necessary to carry out color photographic development processing upon exposure. The color photographic development processing fundamentally comprises steps of color development, bleaching and fixation. Two steps may be carried out by one processing. A combination consisting of color development, first fixation and bleach-fixation can also be adopted. The development processing steps are combined, if necessary, with steps such as prehardening bath, neutralization bath, first development (black-and-white development), image stabilizing bath or water wash. The processing temperature is often 18° C. or more. A particularly used temperature is in the range of 20° C. to 60° C., and more particularly in the range of 30° C. to 60° C.

The color developing solution is an aqueous alkali solution containing an aromatic primary amine color developing agent having a pH of 8 or more, preferably 9 to 12. Preferred examples of the above described color developing agents include 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfonamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfonamidoethyl-N,N-diethylaniline and salts thereof (for example, sulfates, hydrochlorides, sulfites and p-toluenesulfonates). In addition, there are those described in U.S. Pat. Nos. 2,193,015 and 2,592,364, Japanese Patent Application (OPI) No. 64933/73 and "Photographic Processing Chemistry", written by L. F. A. Mason (Focal Press-London, 1966), pages 226–229.

The color developing solution may contain pH buffer agents such as sulfites, carbonates, borates and phosphates of alkali metals, development restrainers or antifogging agents such as bromides, iodides or organic antifogging agents, and fluorescent whitening agents, besides the color developing agent.

Examples of antifogging agents include not only potassium bromide, potassium iodide and nitrobenzimidazoles described in U.S. Pat. Nos. 2,496,940 and 2,656,271, but also mercaptobenzimidazoles, 5-methylbenzotriazoles, 1-phenyl-5-mercaptotetrazoles, compounds described in U.S. Pat. Nos. 3,113,864, 3,342,596, 3,295,976, 3,615,522 and 3,597,199, thiosulfonyl compounds described in British Pat. No. 972,211, phenazine-N-oxides described in U.S. Pat. No. 3,642,481, and antifogging agents described in "Kagaku Shashin Binran" Vol. 2, pages 29–47.

If necessary, it may contain water softeners, preservatives such as hydroxylamine, organic solvents such as benzyl alcohol or diethylene glycol, development accelerators such as polyethylene glycol, quaternary ammonium salts or amines, dye forming couplers, competitive couplers, fogging agents such as sodium boron hydride, auxiliary developing agents such as 1-phenyl-3-pyrazolidone, and thickeners.

The color photographic light-sensitive materials of the present invention are processed by a conventional color development processing, but color intensification development processings as described in the following may be applied. For example, a process using peroxides described in U.S. Pat. Nos. 3,674,490, 3,761,265, 3,765,890 and 3,776,730, Japanese Patent Application (OPI) Nos. 13334/77, 13335/77 and 13336/77, and British Pat. No. 1,341,719, a process using cobalt complex salts described in U.S. Pat. Nos. 4,040,834 and 4,045,226, German Patent Application (OLS) No. 2,226,770 and Japanese Patent Application (OPI) Nos. 9728/73, 9729/73, 6026/76, 133023/76 and 7728/77, and a process using chlorous acid described in Japanese Patent Publication No. 14625/77 and Japanese Patent Application (OPI) Nos. 99022/76 and 103430/76.

The photographic emulsion layers after color development are generally subjected to a bleaching processing. The bleaching processing may be carried out simultaneously with a fixation processing or may be carried out separately. As bleaching agents, compounds of polyvalent metal such as iron (III), cobalt (III), chromium (VI) and copper (II), peracids, quinones and nitroso compounds, are used. For example, it is possible to use ferricyanides, bichromates, organic complex salts of iron (III) or cobalt (III). Complex salts of aminopolycarboxylic acids such as ethylenediaminetetraacetic acid, nitrilotriacetic acid or 1,3-diamino-2-propanol tetraacetic acid, or organic acids such as citric acid, tartaric acid or malic acid; persulfates, permanganates and nitrosophenol are useful. It is particularly preferred to use potassium ferricyanide, sodium ethylenediaminetetraacetato iron (III) and ammonium ethylenediaminetetraacetato iron (III). The ethylenediaminetetraacetato iron (III) complex salts are useful for not only the bleaching solution but also as a one-bath bleach-fixation solution.

To the bleaching solution or the bleach-fixation solution, it is possible to add various additives including bleach accelerators described in U.S. Pat. Nos. 3,042,520 and 3,241,966 and Japanese Patent Publication Nos. 8506/70 and 8836/70.

While the invention has been described in detail and with reference to specific embodiment thereof, it will be apparent to one skilled in the art that various changes and modifications can be made therein without departing from the spirit and scope thereof.

What is claimed is:

1. A silver halide color photographic light-sensitive material comprising a base having thereon at least one photographic layer containing a compound represented by the following general formula:

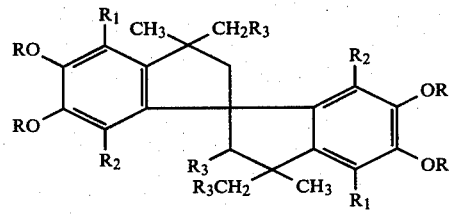

where R represents an alkyl group or an alkenyl group, $R_1$ and $R_2$ each represent hydrogen, a halogen atom, an alkyl group, an aralkyl group, an alkenyl group, an alkoxy group or an alkenoxy group, and $R_3$ represents hydrogen, an alkyl group, an aralkyl group, an alkenyl group or an aryl group, wherein $R_4$, $R_5$ and $R_6$ each represent an alkyl group, an aralkyl group, an alkenyl group, an aryl group or a heterocyclic group.

2. A silver halide color photographic light-sensitive material as claimed in claim 1 wherein R represents an alkyl group or an alkenyl group, and in addition, either one of $R_1$ and $R_2$ represents hydrogen.

3. A silver halide color photographic light-sensitive material as claimed in claim 1 wherein said photographic layer is selected from coupler-contained silver halide photographic light-sensitive emulsion layers and photographic light-insensitive auxiliary layers adjacent thereto.

4. A silver halide color photographic light-sensitive material as claimed in claim 1 wherein said photographic layer is a silver halide photographic light-sensitive emulsion layer containing magenta couplers or cyan couplers.

5. A silver halide color photographic light-sensitive material as claimed in claim 4 wherein said magenta coupler is 5-pyrazolone type couplers.

6. A silver halide color photographic light-sensitive material as claimed in claim 4 wherein said cyan coupler is phenol or naphthol derivatives.

7. A silver halide color photographic light-sensitive material as claimed in claim 3, 4, 5 or 6 wherein said compound is used in an amount of the range of 0.5 to 200% by weight based on couplers.

8. A silver halide color photographic light-sensitive material as claimed in claim 3, 4, 5 or 6 wherein said compound is used in an amount of the range of 2 to 150% by weight based on couplers.

9. A silver halide color photographic light-sensitive material as claimed in claim 1 wherein said compound is used together with antihalation agents selected from hydroquinone derivatives, hydroxychroman derivatives, hydroxyspirochroman derivatives, derivatives of hydroxychroman or hydroxyspirochroman wherein the hydroxy group is converted into an alkoxy group, or alkoxy phenol derivatives.

* * * * *